US006756339B1

(12) United States Patent
Rokicki et al.

(10) Patent No.: US 6,756,339 B1
(45) Date of Patent: Jun. 29, 2004

(54) DEHYDROGENATION CATALYSTS

(75) Inventors: Andrzej Rokicki, Prospect, KY (US); Dennis Smith, Jeffersontown, KY (US); David L. Williams, Louisville, KY (US)

(73) Assignees: Sud-Chemie Inc., Louisville, KY (US); Sud-Chemie Catalysts Japan, Inc., Tokyo (JP)

( * ) Notice: Subject to any disclaimer, the term of this patent is extended or adjusted under 35 U.S.C. 154(b) by 145 days.

(21) Appl. No.: 10/230,629

(22) Filed: Aug. 29, 2002

Related U.S. Application Data

(63) Continuation-in-part of application No. 09/817,399, filed on Mar. 26, 2001, now Pat. No. 6,465,704, which is a continuation of application No. 09/237,408, filed on Jan. 26, 1999, now Pat. No. 6,191,065, which is a continuation-in-part of application No. 09/053,234, filed on Apr. 1, 1998, now Pat. No. 6,242,379.

(51) Int. Cl.[7] ............................ B01J 21/00; B01J 23/00; B01J 23/745
(52) U.S. Cl. ................ 502/304; 502/325; 502/330; 502/331; 502/326; 502/338; 502/339; 502/344; 502/345; 502/305; 502/313; 502/317; 502/318; 502/319; 502/321; 502/306; 502/328; 502/341; 502/324; 502/355; 502/350
(58) Field of Search ................ 502/304, 325, 502/330, 331, 326, 338, 339, 344, 345, 305, 313, 317, 318, 319, 321, 306, 328, 341, 324, 355, 350

(56) References Cited

U.S. PATENT DOCUMENTS

| | | | |
|---|---|---|---|
| 2,408,140 A | 9/1946 | Gutzert |
| 2,414,585 A | 1/1947 | Eggertsen et al. |
| 2,426,829 A | 9/1947 | Kearchy |
| 2,866,790 A | 12/1958 | Pitzer |
| 2,866,791 A | 12/1958 | Pitzer |
| 2,870,228 A | 1/1959 | Armstrong et al. |
| 3,084,125 A | 4/1963 | Soderquist et al. |
| 3,360,579 A | 12/1967 | Hills et al. |
| 3,364,277 A | 1/1968 | Siem |
| 3,424,808 A | 1/1969 | Brewer et al. |
| 3,437,703 A | 4/1969 | Reitmeier et al. |
| 3,505,422 A | 4/1970 | Brewer et al. |
| 3,584,060 A | 6/1971 | Rausch |
| 3,798,178 A | 3/1974 | Soderquist et al. |
| 3,843,745 A | 10/1974 | Christman et al. |
| 3,872,027 A | 3/1975 | Christman et al. |
| 3,878,131 A | 4/1975 | Hayes |
| 3,900,525 A | 8/1975 | Christman et al. |
| 3,904,552 A | 9/1975 | O'Hara |
| 4,098,723 A | 7/1978 | Riesser |
| 4,134,858 A | 1/1979 | Courty |
| 4,144,197 A | 3/1979 | Riesser |
| 4,191,846 A | 3/1980 | Farha, Jr. et al. |
| 4,376,225 A | 3/1983 | Vora |
| 4,404,123 A | 9/1983 | Chu |
| 4,418,237 A | 11/1983 | Imai |
| 4,433,186 A | 2/1984 | Chu |
| 4,435,607 A | 3/1984 | Imai |
| 4,438,288 A | 3/1984 | Imai |
| 4,467,046 A | 8/1984 | Smith et al. |
| 4,496,662 A | 1/1985 | Chu |
| 4,565,898 A | 1/1986 | O'Hara et al. |
| 4,595,673 A | 6/1986 | Imai et al. |
| 4,628,137 A | 12/1986 | Chu |
| 4,652,687 A | 3/1987 | Imai et al. |
| 4,684,619 A | 8/1987 | Moore |
| 4,691,071 A | 9/1987 | Bricker |
| 4,716,143 A | 12/1987 | Imai |
| 4,717,781 A | 1/1988 | Imai et al. |
| 4,749,674 A | 6/1988 | Dejaifve et al. |
| 4,758,543 A | 7/1988 | Sherrod et al. |
| 4,764,498 A | 8/1988 | Wissner et al. |
| 4,786,625 A | 11/1988 | Imai |
| 4,804,799 A | 2/1989 | Lewis et al. |
| 4,806,624 A | 2/1989 | Herber et al. |
| 4,827,066 A | 5/1989 | Herber et al. |
| 4,827,072 A | 5/1989 | Imai et al. |
| 4,902,849 A | 2/1990 | McKay et al. |
| 4,914,249 A | 4/1990 | Benedict |
| 4,926,005 A | 5/1990 | Olbrich et al. |
| 4,975,407 A | 12/1990 | Dejaifve et al. |
| 5,017,543 A | 5/1991 | De Clippeleir et al. |
| 5,023,225 A | 6/1991 | Williams et al. |
| 5,097,091 A | 3/1992 | Kremer et al. |

(List continued on next page.)

FOREIGN PATENT DOCUMENTS

| | | |
|---|---|---|
| CN | 1062678 | 7/1992 |
| CN | 1145277 | 3/1997 |
| WO | WO 96/18458 | 6/1996 |
| WO | WO 96/18593 | 6/1996 |
| WO | WO 96/18594 | 6/1996 |
| WO | WO 97/18034 | 11/1999 |

OTHER PUBLICATIONS

Kirk Othmer, *Encyclopedia of Chemical Technology*, Second Edition, vol. 19, p. 67, No Date.

Atkins, M.P., *A Review of Current Processes and Innovations*, Petrochemie, pp. 271,3 (Jun. 1995).

(List continued on next page.)

*Primary Examiner*—Kiley Stoner
*Assistant Examiner*—Christina Ildebrando
(74) *Attorney, Agent, or Firm*—Scott R. Cox; Joan L. Simunic

(57) ABSTRACT

A catalyst for the nonoxidative production of alkenylaromatics from alkylaromatics, wherein the catalyst is predominantly iron oxide, an alkali metal compound, copper oxide, cerium oxide and less than about 100 ppm of a source for a noble metal, such as palladium, platinum, ruthenium, rhenium, osmium, rhodium or iridium. Additional components of the catalyst may include compounds based on molybdenum, tungsten, calcium, magnesium, chromium and other such promoters.

26 Claims, 1 Drawing Sheet

U.S. PATENT DOCUMENTS

| | | |
|---|---|---|
| 5,190,906 A | 3/1993 | Murakami et al. |
| 5,354,936 A | 10/1994 | Yamamura et al. |
| 5,376,613 A | 12/1994 | Dellinger et al. |
| 5,510,552 A | 4/1996 | Dellinger et al. |
| 5,618,974 A | 4/1997 | Kurimoto et al. |
| 5,668,075 A | 9/1997 | Milam et al. |
| 5,689,023 A | 11/1997 | Hamilton, Jr. |
| 5,744,015 A | 4/1998 | Mazanec et al. |
| 5,830,425 A | 11/1998 | Schneider et al. |
| 6,177,602 B1 | 1/2001 | Williams et al. |
| 6,191,065 B1 | 2/2001 | Williams et al. |
| 6,242,379 B1 | 6/2001 | Williams et al. |
| 6,465,704 B2 | 10/2002 | Williams et al. |

OTHER PUBLICATIONS

Atkins, M.P., *Catalytic Dehydrogenation: A Review of Current Processes and Innovations*, DGMK—Conference, pp 201, 204–5 (1993).

"Encyclopedia of Chemical Processing and Design," McKetta, J.J., Editor, pp 285–6, no date.

Figure 1    Ethylbenzene Dehydrogenation Stability Test Data
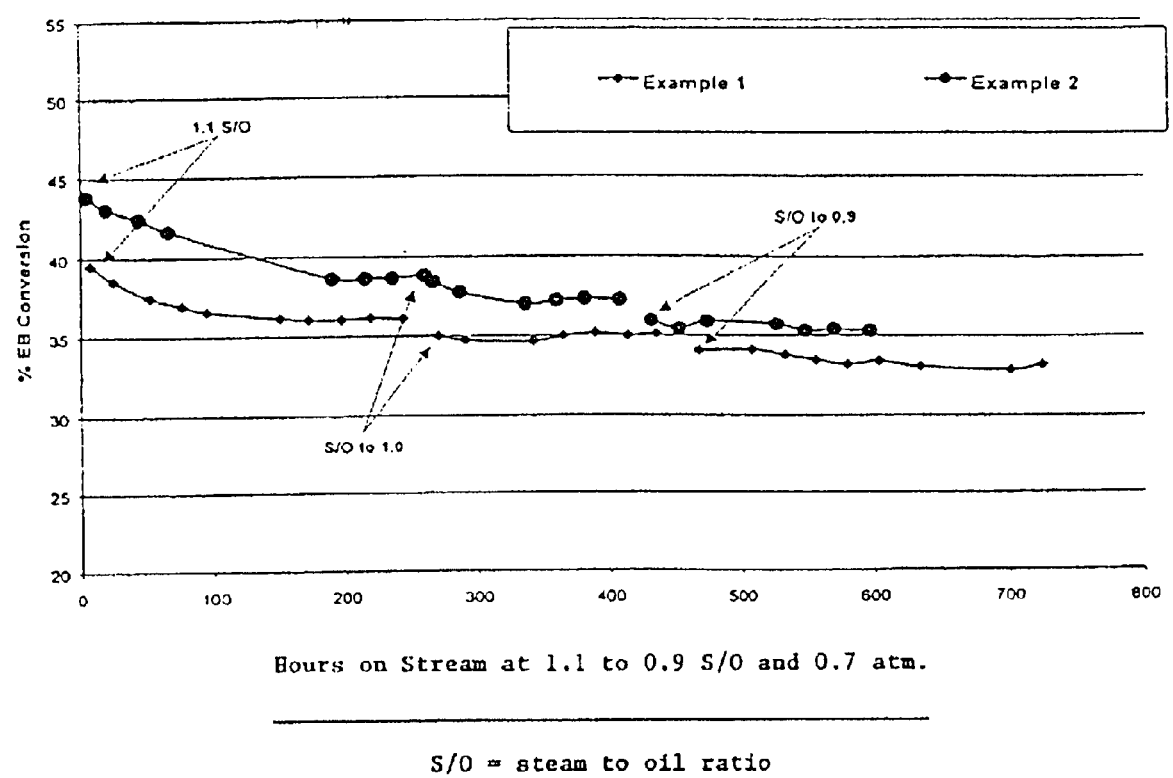
Hours on Stream at 1.1 to 0.9 S/O and 0.7 atm.
S/O = steam to oil ratio

DEHYDROGENATION CATALYSTS

CROSS-REFERENCE TO RELATED APPLICATION

This application is a continuation-in-part of application Ser. No. 09/817,399, filed Mar. 26, 2001 now U.S. Pat. No. 6,465,704, which was a continuation of application Ser. No. 09/237,408, filed Jan. 26, 1999, now U.S. Pat. No. 6,191,065, which was a continuation-in-part of application Ser. No. 09/053,234, filed Apr. 1, 1998, now U.S. Pat. No. 6,242,379.

BACKGROUND OF THE INVENTION

The field of art to which this invention pertains is non-oxidative dehydrogenation catalysts.

In the catalytic dehydrogenation of alkylaromatic hydrocarbons to alkenylaromatic hydrocarbons, e.g., the dehydrogenation of ethylbenzene to styrene, considerable efforts have been expended to develop catalysts which exhibit high conversion combined with high selectivity and increased stability.

Promoted iron oxide catalysts have been found to be especially useful in the dehydrogenation of alkylaromatic hydrocarbons to alkenylaromatic hydrocarbons. Typical commercial iron oxide-based dehydrogenation catalysts are generally promoted with the addition of other metal compounds, in the form of, but not limited to, oxides, hydroxides, carbonates, nitrates, etc. Often one of the promoters is an alkali metal compound with potassium being preferred. Other components may also be added to the dehydrogenation catalyst to provide further promotion, activation or stabilization. In all such dehydrogenation catalysts, minor amounts of modifiers are also typically present, such as organic burn-out agents: carbon black, graphite, methylcellulose, etc., which can beneficially effect the pore structure and/or other physical properties of the catalyst. (In the discussion of the different metal groups, the reference will be based on the new IUPAC notation of the periodic table.)

Typical catalysts used in dehydrogenation of saturated hydrocarbons to unsaturated hydrocarbons, as disclosed in U.S. Pat. No. 2,866,790, are iron oxide catalysts containing a small amount of chromium oxide as a stabilizer and a small amount of potassium compound as promoter. Improved catalysts according to this patent are made from iron oxide (39 to 47 weight percent), chromium oxide (1 to 10 weight percent), and potassium carbonate (51 to 59 weight percent).

Dehydrogenation catalysts having good physical strength are described in U.S. Pat. No. 2,866,791. These catalysts are made from 51 to 59 weight percent potassium fluoride, 1.0 to 10 weight percent chromium oxide with the balance being iron oxide (39 to 47 weight percent).

Catalysts designed for the dehydrogenation of alkylbenzenes, at elevated temperatures in the presence of steam, comprising iron oxide and as a promoter from about 1 to about 25 percent by weight of an alkali metal oxide, from about 1 to about 10 percent by weight of a rare earth metal oxide, and from about 0.1 to about 10 percent by weight calcium oxide, are disclosed in U.S. Pat. No. 4,749,674.

Another catalyst for the dehydrogenation of ethylbenzene to styrene disclosed in U.S. Pat. No. 5,510,552 contains at least one iron oxide, at least one bicarbonate, oxide or hydroxide of potassium and/or cesium, an oxide, carbonate, nitrate or hydroxide of cerium, a hydraulic cement, from about 0.2 to about 10 percent of a sodium oxide and from about 1.5 to about 20 percent calcium oxide. Additional additives for the catalyst may include compounds of chromium, molybdenum, aluminum, vanadium, cobalt, cadmium, copper, magnesium, manganese, or nickel.

Chinese Patent No. 95111761 discloses a dehydrogenation catalyst for alkyl aromatics comprising a mixture of iron, potassium and chromium blended with a pore former binder and colloidal silica. To this mixture may be added metal oxides selected from at least one of Groups IB–VIIIB and IIIA–VIA of the periodic chart. Metal oxides disclosed in the examples include oxides of magnesium, cobalt, copper, lead, bismuth, boron, titanium, nickel, tungsten, zinc, tin, aluminum and palladium.

WO 96/18458 discloses a method of preparing an iron oxide catalyst comprising contacting an iron oxide with a additive comprising an element selected from a large group of elements on the periodic chart, heating that iron oxide mixture to a temperature of at least about 600°, to afford structural rearrangement of the particle habit of said iron oxide, and then forming it into the catalyst. See also WO 96/18594 and WO 96/18593.

Similarly, U.S. Pat. No. 5,668,075 discloses the preparation of improved selectivity iron oxide dehydrogenation catalysts based on reconstructed iron oxides. The reconstruction of the oxides comprises contacting an iron oxide with a dopant substance comprising elements selected from a large group of components of the periodic chart and heating the doped iron oxide to a temperature of at least about 600° C., preferably between 800° C. and 1100° C. Rearrangement of particle habit is induced in iron oxide prior to it being formed into catalyst. The disclosed metal additives are solely and specifically used to promote the physical transformation of the iron oxide and not the chemical properties of the catalyst.

Another dehydrogenation catalyst, which contains smaller amounts of iron oxide and relatively larger amounts of cerium oxide and potassium carbonate, is disclosed in U.S. Pat. No. 4,758,543. Catalysts having good activity and good selectivity are described in U.S. Pat. No. 3,904,552. These catalysts are made with iron oxide and alkali metal oxides plus molybdenum oxide and cerium oxide. Similar catalysts utilizing tungsten oxide in place of molybdenum oxide are described in U.S. Pat. No. 4,144,197.

Dehydrogenation catalysts which maintain high activity and selectivity over extended periods of time are described in U.S. Pat. No. 4,467,046. These catalysts contain iron oxide, an alkali metal compound, a cerium compound, a molybdenum compound and a calcium compound.

Improving stability of Fe/K/Ce/Mo/Ca/Mg oxide catalysts by incorporation of small amounts of chromium (100 to 5000 ppm) prior to forming the catalyst is taught in U.S. Pat. No. 5,023,225.

The addition of titanium also results in improved activity and selectivity of iron oxide/potassium oxide catalytic systems, for ethylbenzene to styrene dehydrogenation, according to U.S. Pat. No. 5,190,906.

Dehydrogenation catalysts made from iron oxide, chromium oxide and kaolinite plus potassium oxide are disclosed in U.S. Pat. No. 4,134,858. The catalysts can also contain at least one oxide of copper, vanadium, zinc, magnesium, manganese, nickel, cobalt, bismuth, tin, or antimony. See also U.S. Pat. Nos. 5,354,936 and 5,376,613.

A dehydrogenation catalyst containing iron and promoted with potassium, cerium and a copper compound is disclosed by U.S. Pat. No. 4,804,799.

U.S. Pat. Nos. 3,424,808 and 3,505,422 are directed to combined dehydrogenation and methanation catalysts which consist essentially of iron oxide, a minor amount of an alkali metal hydroxide or carbonate, and a minor amount of transition metal, preferably ruthenium, cobalt, or nickel.

Catalysts for the dehydrogenation of para-ethyltoluene to para-methylstyrene are described in U.S. Pat. Nos. 4,404,123; 4,433,186; 4,496,662; and 4,628,137. These catalysts are made with iron oxide and potassium carbonate, plus chromic oxide, gallium trioxide, or magnesium oxide. Each patent also discloses that the catalysts can optionally contain compounds of cobalt, cadmium, aluminum, nickel, cesium, and rare earth elements as stabilizers, activators and promoters.

Other dehydrogenation catalysts and procedures for their use and manufacture are shown in U.S. Pat. Nos. 2,408,140; 2,414,585; 3,360,579; 3,364,277; and 4,098,723.

Dehydrogenation reactions are normally conducted at the highest practical throughput rates to obtain optimum yield. Yield is dependent upon conversion and selectivity of the catalyst.

Selectivity of the catalyst is defined as the proportion of the desired product, e.g., styrene, produced to the total amount of feedstock, e.g., ethylbenzene, converted. Activity or conversion is that portion of the feedstock which is converted to the desired product and by-products.

Improvements in either selectivity or activity can result in substantially improved operating efficiency. Higher activity catalysts, for example, allow operation at lower temperatures for any given conversion than do conventional catalysts. Thus, in addition to high energy efficiency, catalysts with high activity are expected to last longer and generate less thermal by-products.

To reduce the amount of carbonaceous residues that are produced during dehydrogenation reactions, steam is added to the hydrocarbon reactant feed with steam to hydrocarbon ratios ranging from about 0.5 to about 18:1 depending on the type of hydrocarbon compound being dehydrogenated. While lower steam to oil ratios are preferably for high performance, higher steam to oil ratios are often necessary with some dehydrogenation catalysts because of the risk of carbon build up.

The ratio of benzene to toluene, B/T ratio, in the final product is another criteria to be used in determining effectiveness of the catalyst. While the benzene by-product produced can be recycled for later processing, toluene can not be easily recycled and is considered an undesirable by-product. Thus catalysts yielding higher B/T by-product ratios, all other factors being the same, are preferred.

Because of various deficiencies in existing catalysts, it is an object of the invention to provide a novel nonoxidative dehydrogenation catalyst with improved performance.

It is another object of the invention to provide an improved nonoxidative dehydrogenation catalyst having both high activity and selectivity.

It is another object of the invention to provide an improved nonoxidative dehydrogenation catalyst with good activity even at low steam to oil ratios.

It is another object of the invention to provide an improved nonoxidative dehydrogenation catalyst with good stability.

It is another object of the invention to provide an improved nonoxidative dehydrogenation catalyst containing at least iron oxide, an alkali metal oxide, copper oxide, cerium oxide and a noble metal as a promoter.

It is another object of this invention to provide an improved nonoxidative dehydrogenation catalyst containing at least iron oxide, an alkali metal oxide, a copper oxide, cerium oxide, and a noble metal, wherein the amount of the noble metal present in the catalyst is less than about 1000 ppm, preferably less than 100 ppm and most preferably less than about 50 ppm.

It is still a further object of this invention to provide an improved process for the production of olefinic compounds, particularly styrene.

These and other objects are obtained by the product and process of the present invention.

SUMMARY OF THE INVENTION

The catalyst of this invention is an improved nonoxidative dehydrogenation catalyst, preferably for use in the nonoxidative dehydrogenation of ethylbenzene to styrene, comprised of about 30 to about 90 weight percent of at least one iron compound, about 1 to about 50 weight percent of a compound selected from the group consisting of oxides, hydroxides, carbonates and bicarbonates of alkali metals, from about 0.1 to about 50 weight percent of an oxide of copper, calculated as CuO, from about 10 to about 60 weight percent of an oxide of cerium, calculated as $Ce_2O_3$ and about 0.1 ppm to about 1000 ppm of at least one of the noble metals, wherein said weight percents are based on the total catalyst weight. Preferably, the noble metal is selected from platinum, palladium, rhodium, ruthenium, rhenium, osmium, and iridium, most preferably platinum or palladium. Preferably, the amount of the noble metal present in the catalyst is less than about 300 ppm. For palladium, platinum, rhenium and rhodium the amount of metal present is more preferably less than about 100 ppm, and most preferably less than 50 ppm. In addition, preferably, the catalyst also contains one or more of the compounds selected from molybdenum or tungsten, magnesium or calcium, a Group IV metal, preferably titanium, and chromium.

The invention is also directed to an improved process for the production of olefinic compounds by nonoxidative dehydrogenation, utilizing the above-described catalyst.

The invention is also directed to an improved process for the production of styrene from ethylbenzene utilizing the above-described catalyst.

BRIEF DESCRIPTION OF THE DRAWING

FIG. 1 compares the performance of a nonoxidative dehydrogenation catalyst containing copper prepared with and without a noble metal as an additive.

DESCRIPTION OF THE INVENTION

The catalysts of this invention are made by combining an iron compound, such as iron oxide or a ferrite, preferably potassium ferrite, with an alkali metal source, which can be in the form of, but is not limited to, oxides, hydroxides, carbonates, nitrates or bicarbonates, preferably a sodium or potassium derivative, and most preferably potassium carbonate, a source for copper, a source for cerium and a source for a noble metal. For purposes of the present invention, the term "noble metal" includes platinum, palladium, rhodium, ruthenium, rhenium, iridium and osmium, with rhodium, ruthenium, platinum and palladium preferable based on performance alone. Based on cost and product availability factors only, palladium and ruthenium are more preferred than platinum, rhodium and rhenium, and to an even greater extent, iridium and osmium are less preferred. The source for the noble metal may include elemental noble metal, compounds containing the noble metal or combinations thereof.

In addition to the above-described components, the catalyst may also include as a promoter an oxide or salt of the lanthanides having atomic number of 57 to 62 other than cerium, although cerium is preferred.

The catalyst preferably also includes molybdenum or tungsten compounds, preferably oxides, most preferably molybdenum oxide. The catalyst preferably also includes alkaline earth metal compounds, most preferably magnesium oxide or calcium oxide. The catalyst may also include a source for titanium, chromium or silicon or aluminum, preferably an oxide or salt. The catalyst may also include a source for at least one of the following elements including zinc, manganese, cobalt and vanadium and combinations thereof.

In a preferred embodiment, the catalyst of this invention is composed of about 30 to about 90 weight percent iron oxide calculated as $Fe_2O_3$, about 1 to about 50 weight percent of the oxide, hydroxide, carbonate, or bicarbonate of an alkali metal, calculated as an oxide, from about 0.1 to about 50 weight percent of copper oxide, calculated as CuO, from about 10 to about 60 weight percent of cerium oxide, calculated as $Ce_2O_3$, and from about 0.1 to about 1000 ppm of a noble metal, wherein the noble metal is preferably platinum, palladium, ruthenium, rhodium or iridium, wherein said weight percents are based on the total catalyst weight. Preferably the amount of the noble metal present is from about 0.1 to about 300 ppm. For palladium, rhenium and rhodium the amount of metal is more preferably from about 0.1 to about 100 ppm, and most preferably from about 0.1 to about 50 ppm. Preferably, the catalyst also contains as promoters one or more of the Hollowing: from about 0.5 to about 10 weight percent molybdenum oxide or tungsten oxide calculated as $MoO_3$ or $WO_3$, and from about 0.2 to about 10 weight percent an alkaline earth metal oxide, preferably magnesium or calcium oxide. Additional components of the catalyst may include from about 50 ppm to about 4 weight percent of chromium oxide calculated as $Cr_2O_3$ and from about 10 ppm to about 2000 ppm of titanium oxide calculated as $TiO_2$. The catalyst may also include from about 0.1 to about 10 weight percent of the salt or oxide of one or more of the following: aluminum, silicon, zinc, manganese, cobalt, cadmium and vanadium, alone or in combination, calculated on an elemental basis.

A particularly effective nonoxidative dehydrogenation catalyst contains from about 40 to about 90 weight percent iron oxide calculated as $Fe_2O_3$, from about 5 to about 20 weight percent of an alkali metal compound calculated as an alkali metal oxide, from about 1 to about 15 weight percent of copper oxide, calculated as CuO, from about 12 to about 30 weight percent cerium oxide, calculated as $Ce_2O_3$, and from about 1 ppm to about 100 ppm of a source of a noble metal, wherein the noble metal is preferably palladium, platinum, rhenium, rhodium, ruthenium or iridium. For palladium, rhenium and rhodium preferably the amount of metal present is from about 0.1 to about 100 ppm, most preferably from about 0.1 to about 50 ppm. The source for the noble metal is selected from the group including elemental noble metals, preferably elemental palladium, elemental rhodium, elemental ruthenium, elemental platinum and elemental iridium, compounds containing noble metals, preferably compounds containing palladium and/or ruthenium and/or rhodium and/or platinum and/or iridium and combinations thereof. The catalyst also preferably includes from about 0.5 to about 10 weight percent of a molybdenum or tungsten compounds calculated as $MoO_3$ or $WO_3$, wherein all weight percents are based on the total weight of the catalyst. Additional promoters may be included with this catalyst as discussed above.

A most preferable nonoxidative dehydrogenation catalyst contains from about 40 to about 90 percent iron oxide calculated as $Fe_2O_3$, about 5 to about 20 percent of an alkali metal compound, preferably potassium oxide, about 1 to about 15 weight percent copper oxide calculated as CuO, about 12 to about 30 percent of cerium oxide calculated as $Ce_2O_3$, about 0.5 to about 10 percent of molybdenum or tungsten oxide calculated as $MoO_3$ or $WO_3$, preferably molybdenum oxide, about 0.2 to about 10 percent of calcium or magnesium oxide, preferably calcium oxide, about 10 ppm to about 1000 ppm of titanium oxide calculated as $TiO_2$, about 100 ppm to about 2000 ppm of chromium oxide calculated as $Cr_2O_3$, and from about 0.1 to about 20 ppm of a source for a noble metal, wherein the noble metal is preferably palladium, ruthenium, rhodium, platinum and/or iridium, and wherein the percentage is calculated on an elemental basis. Additional components that can be added to this catalyst include from about 0.1 to about 10.0 weight percent of an oxide of aluminum, silicon, manganese, zinc, cadmium, vanadium, and cobalt, calculated on an elemental basis.

It is advantageous to prepare the catalyst using one or a combination of the following methods: co-precipitation, decomposition, impregnation and mechanical mixing or any other method, as would be readily appreciated by those skilled in the art. The method chosen should guarantee intimate mixing and uniform distribution of the components.

It is well established in the art that different forms of iron oxide, red, yellow, brown and black, can be used for preparation of the nonoxidative dehydrogenation catalyst. Likewise, it is known in the art that the iron oxides can be derived from a variety of precursor materials, both natural and synthetic, using a number of processes. Generally, iron is added to the catalyst compositions as red iron oxide, $Fe_2O_3$, or yellow iron oxide, $Fe_2O_3 \cdot H_2O$, but others can be readily utilized as would be appreciated by those skilled in the art. Particularly suited are pigment grades of the iron oxides. Ferrites may also be used, such as potassium ferrite.

Likewise, the catalyst promoter can include any material taught by the art, for example, an alkali metal compound(s). Potassium compounds are the preferred alkali metal promoters. The promoter can be added to the catalyst in various forms. Alkali metal oxides, hydroxides, carbonates, bicarbonates, and the like, and mixtures thereof are preferred, with potassium carbonate or a mixture of potassium carbonate with potassium oxide is most preferred.

The catalyst compositions of the present invention contain compounds of copper which improve activity, enhance stability and produce a nonoxidative dehydrogenation catalyst that performs well in low steam to oil ratios. The copper can be added to the catalyst formulation in the form of oxides, hydroxides, carbonates, acetates, nitrates or sulfate or the like. For example, copper may be added in the manner taught by U.S. Pat. No. 4,804,799, which patent is incorporated herein by reference.

The catalyst compositions of the present invention preferably contain compounds of cerium to enhance conversion and/or selectivity depending on the co-promoters. Cerium can be added to the catalyst in the form of cerium oxide or in the form of other cerium compounds, as for example, cerium carbonate, cerium nitrate, cerium hydroxide, or any combination thereof.

Other known catalyst additives can also be included in the catalysts of the present invention, but are not essential. A chromium compound, which can serve as a stabilizer for the active catalytic components, is illustrative of an optional and preferred, additive. Chromium compounds are added to alkali-promoted iron oxide catalysts to extend their life and improve stability at low steam to oil conditions of operation. Chromium, as used in the compositions of the present invention, can be added to the catalyst in the form of a chromium oxide or in the form of a chromium salt. Preferably, chromium is added by spiking of the iron oxide used in catalyst preparation as taught in U.S. Pat. No. 5,023,225.

The addition of titanium is taught in U.S. Pat. No. 5,190,906. Other optional components, used to improve selectivity of the catalyst, include molybdenum or tungsten, which can be added as respective oxides or salts, including derivatives of corresponding oxo acids (i.e. molybdates or tungstates, respectively). In addition, a number of other metal compounds may be added as promoters. These can include, but are not limited to, compounds of aluminum, vanadium, cobalt, cadmium, calcium, magnesium, and manganese.

The physical strength, activity and selectivity of the catalyst compositions of the present invention can be improved by adding certain binding agents. Binding agents can include, but are not limited to, hydraulic cements, calcium aluminate or Portland cement. These agents can be added individually or in combination.

The density of the catalyst composition can be modified by the addition of various filler substances, for example, combustible materials such as graphite and methyl cellulose. Such materials can be added to the compositions during preparation, but are burned out after the catalyst pellets have been formed during the calcining step. Porosity promoting aids can also facilitate extrusion of catalyst pellets.

Known methods can be used to form the catalyst mass. Preferred forming methods are pelletizing, extruding and tableting, in which the use of inorganic or organic auxiliaries as lubricants to improve plasticity during extrusion is recommended. Forming can also be undertaken both before and after calcination.

The catalyst components can be mixed in various ways known to the art. One method comprises ballmilling together a mixture of desired compounds, adding a small amount of water, and extruding the composite to produce small pellets, which are then dried and calcined. Another method is mixing the components together with water, drying them to form a powder, and tableting and calcining the tablets. Another procedure involves mixing the components together with an excess of water, partially drying, and then subsequently extruding, drying, and calcining the resulting pellets. The choice of the mixing method depends on the preference of the skilled artisan.

A preferred method of preparing the catalyst is to blend the catalyst ingredients together in the presence of sufficient water to make a moist extrudable mixture. This mixture is then extruded to produce extrudates of desired shape and size, typically cylindrical pellets having a diameter of about 3 mm. The extrudates are then calcined under conventional calcining conditions. Calcination temperatures can range from about 500° C. to about 1200° C., preferably from about 600° C. to about 1000° C. After calcination, the extrudates are ready for use as catalysts.

The efficacy of the noble metal addition is independent of the method of addition or the point in the manufacturing process at which it is incorporated. The following are some methods for delivery of the noble metal promoter. A number of alternative methods would be obvious to one skilled in the art.

The noble metal, preferably palladium, platinum, ruthenium, rhodium or iridium additives, can be directly added to the iron oxide and the mixture can be pre-fired at about 300° C. to about 500° C. prior to blending with the other components. Alternatively, the noble metal, preferably palladium, ruthenium, rhodium, platinum or iridium, can be co-precipitated with iron oxide prior to the iron oxide being blended. In yet another embodiment, the noble metal, preferably palladium, ruthenium, rhodium, platinum or iridium additives can be impregnated onto the surface of the finished catalyst followed by drying and re-calcination at a temperature adequate to drive-off water and decompose the impregnated salt. However, addition of the noble metal, preferably palladium, ruthenium, rhodium, platinum or iridium additives in the form of an aqueous solution of appropriate salts, preferably nitrates, directly to the catalyst blend, immediately prior to mulling and pelletizing, is preferred.

Heat treatment or calcination can be conducted under static conditions, for example, in a tray furnace, or under dynamic conditions, such as in a rotary kiln. The temperatures and residence times are determined for each individual type of catalyst.

The catalysts preferably are formed as moldings, especially in the form of spheres, pellets, rings, tablets or extruded products, in which they are formed as solid or hollow objects in order to achieve a high geometric surface with a simultaneously low resistance to flow.

The BET surface area of the catalysts is typically about 0.5 to about 12 $m^2/g$, and preferably, about 1.5 to about 4 $m^2/g$. The BET surface area is determined by $N_2$ adsorption, as described in ASTM D3663-92.

The specific pore volume is determined according to the mercury penetration method described in J. Van Brakel, et al., Powder Technology, 29, p.1 (1981). In this method, mercury is pressed up to a pressure of about 4000 bar into the catalyst moldings, during which the volume reduction of the mercury is plotted as a function of pressure. A curve is obtained from which the pore distribution can also be determined. According to this mercury penetration method, only the volume and distribution of pores with a diameter of >3.6 nm can be determined. Generally, catalysts with larger pore volume and higher median pore diameter are preferred as taught in U.S. Pat No. 5,689,023. Typical pore volume of the catalysts of the present invention is in the range of ca. 0.10 to 0.45 cc/g.

One skilled in the art will readily appreciate that surface area, total pore volume and pore volume distribution can be adjusted with proper manufacturing techniques to get optimum performance for any given catalyst composition. This notwithstanding, the promotional effect of noble metals, preferably palladium, ruthenium, rhodium or iridium; addition to the formulations is still unmistakable.

The catalysts of the present invention are effective as nonoxidative dehydrogenation catalysts and especially effective in promoting the nonoxidative dehydrogenation of ethylbenzene to produce styrene. Such nonoxidative dehydrogenation reactions are generally carried out at reaction temperatures from about 480° C. to about 700° C., preferably about 535° C. to about 650° C. The use of subatmospheric, atmospheric, or superatmospheric pressures are suitable for the reactions. However, based on equilibrium and selectivity considerations, it is preferred to operate at as low a pressure as is feasible. Therefore, atmospheric or subatmospheric pressure is preferred. Typically the nonoxidative dehydrogenation process using the catalysts of this invention is conducted as a continuous operation utilizing a fixed bed which may consist of a single stage or a series of stages of the same or different catalysts in one or more reactors. Other types of reactors and reactor configurations can be used for the dehydrogenation process.

In the nonoxidative dehydrogenation process using the catalyst of this invention, steam is added to the hydrocarbon feedstock to aid in the removal of carbonaceous residues from the catalyst and to furnish heat for the reaction. Steam to hydrocarbon molar ratios from about 3 to about 18 or higher can be used. However, in order to conserve energy in the operation of the process, steam to hydrocarbon molar ratios (S/O) of 12 or lower are preferred. It has been surprisingly discovered that the catalyst of the invention performs well at low S/O ratios.

The contact time of the reactant-containing gas with the catalyst is expressed in terms of liquid-hourly-space velocity (LHSV) which is defined as the volume of liquid hydrocarbon reactant per volume of catalyst per hour. The LHSV of the organic reactants can vary between about 0.1 hour$^{-1}$ and about 5 hour$^{-1}$.

It has been surprisingly discovered that extremely small quantities of noble metals when added to the catalyst result in enhanced performance and selectivity. In fact, it has been surprisingly discovered that smaller quantities of the noble metals (less than 1000 ppm) are more effective than larger quantities of noble metals (greater than 5000 ppm). Thus, a better performing catalyst is produced when the quantity of the catalyst is less than 1000 ppm, preferably less than 300 ppm. For palladium, rhenium and rhodium the amount of metal present is preferably less than 100 ppm, and most preferably less than 50 ppm. It has also been surprisingly discovered that extremely small quantities (from 0.01 ppm to about 50 ppm) perform as well as larger quantities, such as quantities greater than about 5000 ppm.

When used in the continuous process of nonoxidative dehydrogenating ethylbenzene to styrene, the catalysts of this invention exhibit better performance, i.e. higher conversion, improved yield and higher B/T ratio, than similar catalysts which do not contain noble metals.

EXAMPLES

The following examples describe the invention in more detail. Parts and percentages are by weight unless otherwise designated. Iron oxide used in all the following preparations is a commercial product that may contain ppm levels of Ti and Cr and may also contain minor amounts of other elements such as Si, Al, Mn, Mg, S, Cl, Zn, V, Cu, etc.

Example 1

687 grams of red iron oxide, 780 grams of yellow iron oxide, 1400 grams of potassium carbonate, 1375 grams of cerium carbonate, 400 grams of basic copper carbonate, 40 grams of molybdenum trioxide, 179 grams of gypsum, 127 grams of calcium carbonate, 282 grams of calcium aluminate cement, 105 grams graphite and 53 grams of methocel are dry blended until well mixed. A sufficient quantity of water is added to the mixture to form an extrudable mass. The mixture is mulled together for about 20 minutes and then extruded into pellets of 4.3 mm diameter. The pellets are calcined for several hours at 1500° F. (815° C.)

Example 2

A second catalyst is prepared according to the procedure of Example 1, except that a palladium nitrate solution sufficient to produce a concentration of about 20 ppm of palladium in the calcined catalyst is added to the mixture prior to the mixing of the components of the mixture. The remaining process steps for the process of Example 1 were followed.

The catalysts of Example 1 (Comparative) and Example 2 (Inventive) are tested for performance in the nonoxidative dehydrogenation of ethylbenzene to styrene. The test reactor is a fixed bed type reactor containing a catalyst volume of 100 cc. A mixture of ethylbenzene and steam is passed over the catalyst at 1.0 LHSV, 2.0 steam to ethylbenzene ratio, 1 atmospheric pressure and a temperature sufficient to obtain 50 percent ethylbenzene conversion. Data from the reaction is shown in Table 1.

TABLE I

| Example No. | Temperature of 50% conversion | Percent Selectivity |
| --- | --- | --- |
| 1 | 1085° F. (585° C.) | 97.5 |
| 2 | 1078° F. (581° C.) | 97.2 |

Improved performance of the catalyst according to the invention, Example 2, is evidenced by the lower temperature at which 50 percent conversion occurs.

After the initial testing as described above, additional tests are conducted to determine the performance stability of the catalysts at low steam to hydrocarbon ratios. The temperature is adjusted to 1050° F. (565.5° C.) and the reaction pressure is adjusted to 0.7 atmospheres. Performance is measured as a percentage of conversion of ethylbenzene to styrene in comparison to the time on stream, steam to hydrocarbon ratios between 1.1 and 0.9. The data indicates an improved performance at each steam to hydrocarbon level for the inventive catalyst containing palladium of Example 2 as shown in FIG. 1.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A nonoxidative dehydrogenation catalyst comprising about 30 to about 90 weight percent of an iron compound calculated as $Fe_2O_3$, about 1 to about 50 weight percent of an alkali metal source calculated as an alkali metal oxide, about 0.1 to about 50 weight percent of a copper compound calculated as CuO, about 10 to about 60 weight percent of a cerium compound, calculated as $Ce_2O_3$, and about 0.1 ppm to about 1000 ppm of a noble metal source selected from the group consisting of elemental noble metals, compounds containing noble metals and combinations thereof, wherein all weight percents are based on the total weight of the catalyst.

2. The dehydrogenation catalyst of claim 1 wherein the iron compound comprises iron oxide.

3. The dehydrogenation catalyst of claim 1 wherein the iron compound comprises a potassium ferrite.

4. The catalyst of claim 1 wherein the alkali metal source comprises a potassium compound.

5. The catalyst of claim 1 wherein the alkali metal source comprises potassium carbonate.

6. The catalyst of claim 1 wherein the copper component comprises from about 1 to about 15 weight percent, calculated as CuO, of the catalyst.

7. The catalyst of claim 1 wherein the noble metal is selected from the group consisting of palladium, platinum, rhenium and ruthenium.

8. The catalyst of claim 1 wherein the noble metal source is selected from the group consisting of elemental palladium, elemental ruthenium, elemental platinum, compounds containing palladium, ruthenium and platinum and combinations thereof.

9. The catalyst of claim 1 wherein the cerium compound comprises from about 12 to about 30 weight percent, calculated as $Ce_2O_3$, of the catalyst.

10. The catalyst of claim 1 further comprising from about 50 ppm to about 4 weight percent of a chromium compound, calculated as $Cr_2O_3$.

11. The catalyst of claim 1 further comprising from about 0.5 to about 10 weight percent of a molybdenum or tungsten compound calculated as $MoO_3$ or $WO_3$.

12. The catalyst of claim 1 further comprising from about 0.5 to about 10 weight percent of a molybdenum or tungsten compound, calculated as $MoO_3$ or $WO_3$, and from about 0.2 to about 10 weight percent of a calcium or magnesium compound, calculated as an oxide.

13. The catalyst of claim 1 further comprising from about 0.5 to about 10 weight percent of a molybdenum or tungsten compound calculated as $MoO_3$ or $WO_3$, from about 0.2 to about 10 weight percent of a magnesium or calcium compound, and from about 10 ppm to about 2000 ppm of a source for titanium calculated as $TiO_2$, all weight percents calculated as oxides.

14. The catalyst of claim 1 further comprising from about 0.1 weight percent to about 10 weight percent of a source for at least one of the following elements selected from the group consisting of aluminum, silicon, zinc, manganese, cobalt, vanadium and combinations thereof, all weight percents calculated on an elemental basis.

15. A nonoxidative dehydrogenation catalyst comprising from about 40 to about 90 weight percent iron oxide calculated as $Fe_2O_3$, from about 5 to about 20 weight percent of an alkali metal compound calculated as an alkali metal oxide, from about 1 ppm to about 100 ppm of a noble metal source selected from the group consisting of elemental noble metals, compounds containing a noble metal and combinations thereof, from about 1 to about 15 weight percent of a copper compound calculated as CuO, from about 0.5 to about 10 weight percent of a molybdenum or tungsten compound, calculated as $MoO_3$ or $WO_3$ and from about 12 to about 30 weight percent of a cerium compound, calculated as $Ce_2O_3$, wherein all weight percents are based on the total weight of the catalyst.

16. The catalyst of claim 15 wherein the alkali metal compound comprises a potassium compound.

17. The catalyst of claim 15 wherein the noble metal is selected from the group consisting of palladium, platinum, iridium, rhodium and ruthenium.

18. The catalyst of claim 15 wherein the noble metal source is selected from the group consisting of elemental palladium, elemental platinum, elemental rhodium, elemental ruthenium, elemental iridium, compounds containing palladium, platinum, rhodium, ruthenium and iridium and combinations thereof.

19. The catalyst of claim 15 further comprising from about 10 ppm to about 2000 ppm of a chromium compound.

20. The catalyst of claim 15 further comprising from about 0.2 to about 10 weight percent of a calcium or magnesium compound, calculated as an oxide.

21. The catalyst of claim 15 further comprising from about 10 ppm to about 2000 ppm of a source for titanium, calculated as $TiO_2$.

22. The catalyst of claim 15 further comprising from about 0.1 to about 10 weight percent of a source for at least one of the following elements selected from the group consisting of aluminum, silicon, zinc, manganese, cobalt, vanadium, and combinations thereof, all weight percents calculated on an elemental basis.

23. A nonoxidative dehydrogenation catalyst comprising from about 40 to about 90 weight percent iron oxide calculated as $Fe_2O_3$, from about 5 to about 20 percent of a potassium compound calculated as potassium oxide, from about 0.1 ppm to about 20 ppm of a noble metal source selected from the group consisting of an elemental noble metal, compounds containing a noble metal and combinations thereof, from about 1 to about 15 percent by weight of a copper compound calculated as CuO, from about 0.5 to about 10 weight percent of a molybdenum or tungsten compound calculated as $MoO_3$ or $WO_3$, from about 12 to about 30 weight percent of a cerium compound calculated as $Ce_2O_3$, from about 0.2 to about 10 weight percent of a calcium or magnesium compound calculated as an oxide, from about 100 ppm to about 2000 ppm of a chromium compound calculated as $Cr_2O_3$, and from about 10 ppm to about 1000 ppm of a source for titanium calculated as $TiO_2$, wherein all weight percents are based on the total weight of the catalyst.

24. The catalyst of claim 23 wherein the noble metal is selected from the group consisting of palladium, platinum, rhodium, ruthenium and iridium.

25. The catalyst of claim 23 wherein the source for the noble metal is selected from the group consisting of elemental palladium, elemental platinum, elemental rhodium, elemental ruthenium, elemental iridium, compounds containing palladium, platinum, rhodium, ruthenium and iridium and combinations thereof.

26. The catalyst of claim 23 further comprising from about 0.1 weight percent to about 10 weight percent of a source for at least one of the following elements selected from the group consisting of aluminum, silicon, manganese, cobalt, vanadium, and combinations thereof, calculated on an elemental basis.

* * * * *